United States Patent
Vulto et al.

(10) Patent No.: US 8,431,339 B2
(45) Date of Patent: Apr. 30, 2013

(54) INTEGRATED MICROFLUIDIC COMPONENT FOR PURIFYING ANALYTE MOLECULES AND PURIFICATION METHOD

(75) Inventors: Paul Vulto, Freiburg (DE); Gerald Urban, Freiburg (DE)

(73) Assignee: Albert-Ludwigs-Universitat Freiburg, Freiburg (DE)

( * ) Notice: Subject to any disclaimer, the term of this patent is extended or adjusted under 35 U.S.C. 154(b) by 938 days.

(21) Appl. No.: 12/447,305

(22) PCT Filed: Oct. 26, 2007

(86) PCT No.: PCT/EP2007/009330
§ 371 (c)(1),
(2), (4) Date: Apr. 27, 2009

(87) PCT Pub. No.: WO2008/049638
PCT Pub. Date: May 2, 2008

(65) Prior Publication Data
US 2010/0084270 A1    Apr. 8, 2010

(30) Foreign Application Priority Data
Oct. 27, 2006 (DE) .................... 10 2006 050 871

(51) Int. Cl.
*C12Q 1/68* (2006.01)
*G01N 27/26* (2006.01)

(52) U.S. Cl.
USPC ........ 435/6.1; 435/283.1; 422/68.1; 422/501; 422/527; 204/461; 536/23.1

(58) Field of Classification Search .................. None
See application file for complete search history.

(56) References Cited

U.S. PATENT DOCUMENTS

| 6,129,828 A * | 10/2000 | Sheldon et al. ............... 204/518 |
| 2002/0155586 A1 * | 10/2002 | Cheng et al. ............... 435/287.1 |
| 2003/0070925 A1 * | 4/2003 | Voss ............................. 204/453 |
| 2006/0088867 A1 | 4/2006 | Weir et al. |

FOREIGN PATENT DOCUMENTS

| DE | 297 02 254 | 7/1997 |
| WO | WO 97/41219 | 11/1997 |
| WO | WO 2004/013329 | 2/2004 |

OTHER PUBLICATIONS

Schonhuber, W. et al. "Utilization of tmRNA sequences for bacterial identification" *BMC Microbiology*, Sep. 7, 2001, pp. 1-8, vol. 20, No. 1, XP-021014766.

* cited by examiner

*Primary Examiner* — Betty Forman
(74) *Attorney, Agent, or Firm* — Saliwanchik, Lloyd & Eisenschenk

(57) ABSTRACT

The present invention relates to a method for purifying analyte molecules and in particular to a component of this type in which a separation section is used for separating analyte molecules and other constituents of a sample, and in which provision is made of at least one sample chamber for receiving a sample containing the analyte molecules and at least one collecting chamber for receiving the purified analyte molecules. According to the invention, the microfluidic component has at least one integrated receptor device for detecting the presence and/or the concentration of the purified analyte molecules. In accordance with one advantageous development of the present invention, the separation section is formed by an electrophoretic gel filtration section.

38 Claims, 15 Drawing Sheets

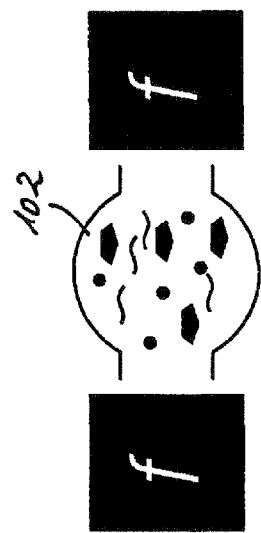
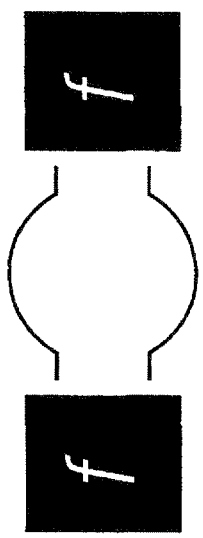
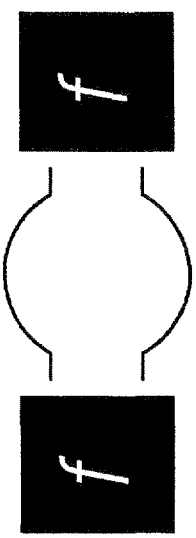
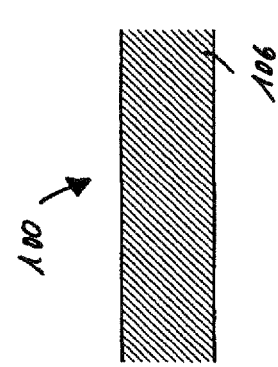
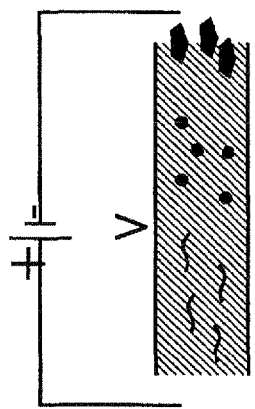
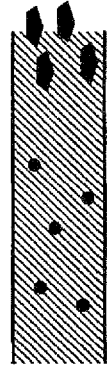
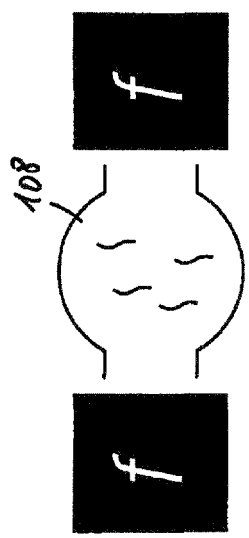
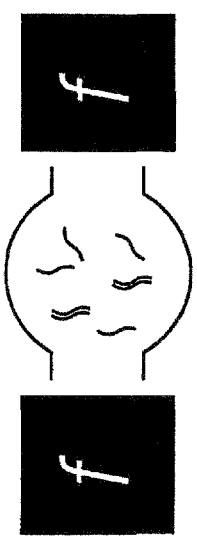
FIG. 4
FIG. 5
FIG. 6

INTEGRATED MICROFLUIDIC COMPONENT FOR PURIFYING ANALYTE MOLECULES AND PURIFICATION METHOD

CROSS-REFERENCE TO RELATED APPLICATION

This application is the U.S. national stage application of International Patent Application No. PCT/EP2007/009330, filed Oct. 26, 2007, the disclosure of which is hereby incorporated by reference in its entirety, including all figures, tables and amino acid or nucleic acid sequences.

The present invention relates to an integrated microfluidic component for purifying analyte molecules and in particular to such a component, in which a separation section for separating analyte molecules and other components of a sample is used, and in which at least one sample chamber is provided for receiving a sample containing the analyte molecules and at least a collecting chamber is provided for receiving the purified analyte molecules.

Such microfluidic components, which are also often designated as a microchip or a microfluidic chip, are known e.g. for DNA extraction from International Patent Application WO 2004/013329 A1. The DNA extraction device according to this document includes a main channel with a first sample current, in which the DNA-containing material, typically bacterial cells or cell fragments, is present. The DNA-containing material is first subject to an electroporation step, in order to release DNA, and the DNA is then introduced into a second parallel current of a second fluid, in order to be separated by means of electroseparation from the undesirable components. Admittedly with this known method, only negatively charged particles may be separated from positively charged or neutral components.

Further, macroscopic separation methods exist for purifying nucleic acids, which are based on the principle of electrophoresis. Examples of such separation methods are illustrated in the Canadian Patent Application published before examination CA 2318973 A1, the published European Patent Application EP 03 824 246 A2, the Canadian Patent document CA 2130751 C, the American Patent document U.S. Pat. No. 5,384,022 as well as the American Patent Application US 2002/0168643 A1.

Document CA 2318973 A1 shows different methods for purifying nucleic acids, using gel electrophoresis in a sample, without however mentioning a detection step or an integrated lysis step.

EP 03 824 246 A2 describes a continuous flow-through electrophoresis system, which may be applied in the preparative purification of nucleic acids on the basis of gel elution. The system is designed for highly efficient purification of similar components such as DNA fragments of different lengths and neither suggests an integrated affinity experiment nor sample preparation steps, such as for example a lysis.

Further, a layout is known from CA 2130751 C, with the help of which after conventional electrophoresis, the different components may be eluted out of the gel. In doing so, the layout is focused on extracting material which was submitted to a first analysis step, in order to submit it to subsequent further analysis. This document is, however, neither concerned with integrated pre-treatment nor with integrated detection.

A device for extracting a DNA band for further analysis is known from U.S. Pat. No. 5,384,022, in which, however, no integrated analysis device is suggested.

American Patent Application US 2002/0168643 A1 finally shows a similar layout for ultra-pure purification, which allows several experiments to be conducted in parallel, but does not enable any integrated detection.

A miniaturized device for purification of nucleic acids by using silicon microstructures is described in Nathaniel C. Cady et al.: "Nucleic acid purification using microfabricated silicon structures" Biosensors and Biolelectronics, 19 (2003) 59-66. Here microstructured columnar geometries are used in a flow-through channel for on-chip purification of DNA before a PCR step. This method is, however, not sufficiently sensitive for direct detection of DNA molecules, so that amplification via a PCR step is always required. Further, the layout shown here has the drawback that a complex actuation scheme is required with external pump systems and that the purification method consists of a plurality of steps, such as an adsorption, a washing step and a desorption step.

Further, there are various publications which indicate a collection of fractions after electrophoretic separation: R. Lin et al.: "Selective extraction of size-fractioned DNA samples in microfabricated electrophoresis devices", J. Chromatography A, 1010 (2003), 255-268, and J. Khandurina et al.: "Micropreparative fraction collection in microfluidic devices", Anal. Chem., 2002, 74, 1737-1740. The goal of these publications was, however, to show conventional electrophoresis on a chip and to subsequently conduct the extraction of the specific separation band for further analyses. Purification in a strict sense did not take place here. Furthermore, the fractions were collected after separation of similar components, for example separation of DNA bands, which ultimately only represents a miniaturization of macrobiological standard procedures.

WO 2006/071770 A2 discloses an extraction method for genomic DNA, which is based on an extraction of a solid phase. According to this document, magnetic beads and filters are used as solid phase carriers, as this is known as a conventional purification method. After purification, a portion of the genomic DNA is amplified by using PCR. The amplified PCR product is then separated from the primers by means of electrophoresis.

Thus, the task which is at the basis of the present invention consists in specifying an integrated microfluidic component for the purification of analyte molecules, which enables fast, sensitive and automatable purification and determination of analyte molecules, for example nucleic acids.

This task is achieved by the object of the independent claims. Advantageous enhancements are the object of the dependent claims.

The present invention is based on the idea of using a microfluidic electrophoresis gel filtration section for purifying the analyte. In addition to a high efficiency and analyte yield, the integrated microfluidic component according to the invention, especially in connection with the detection of ribonucleic acids, RNA, for example transfer-messenger RNA, (tmRNA), provides the advantage of avoiding as far as possible degradation of the sensitive RNA by this enzyme by means of the fast on-chip purification under substantially RNase-free conditions.

According to an advantageous embodiment of the present invention, the separation section is formed by an electrophoretic gel filtration section. For example, a 4% NuSieve-gel may be used. Alternative gel materials are agarose gels, polyacrylamide gels, or a mixture of both. The gels may be applied in denaturating form, i.e. with added amounts of formaldehyde, glycerine, DMSO or urea, but they do not necessarily have to be treated in this way.

By applying a voltage between the beginning and the end of the gel filtration section, the RNA is separated from the remaining sample components according to the known electrophoresis principle. Here, the electrophoresis is based on a combination of size, form and charge of the components to be separated. For example, nucleic acids have a relatively high charge as compared with most proteins. Their shape is rather longitudinal unlike the complex three-dimensional shapes of most proteins. RNA thus has a higher migration rate than most other proteins in an electrophoretic separation matrix. Further, as this generally known, proteins have a positive or negative charge corresponding to their isoelectric points under certain environmental conditions. By cleverly selecting the buffer parameters, such as pH value or ion composition, migration of the proteins in the direction of a desired electrode may be achieved by applying voltage. In particular, RNase enzymes are of interest here.

Filtration is performed until the RNA molecules are substantially eluted out of the gel. Gel electrophoresis in this context provides the advantage of being efficient so that after only one purification step, the analytes exist in a sufficiently pure form for direct hybridization. Thus, a PCR step in particular in connection with naturally amplified RNA molecules, such as tmRNA, may be omitted because of the high extraction and purification yield.

Furthermore, additional increase in efficiency may be achieved by the specific configuration of the gel filtration section. For example, a gel gradient or a sequence of different gels may be provided. The sequence of gels may for example contain gels with decreasing pore size. PH gradients or ionic gradients may also be used inside a gel.

Furthermore, it is possible with the solution according to the invention to perform the purification and detection of purified analyte molecules inside one and the same microfluidic integrated component. An essential advantage of the layout according to the invention is that the direct coupling of the purification with the detection may provide a reproducible and automatable principle for diagnostic analysis.

According to an advantageous embodiment of the present invention, the detection device has a detection unit, for example a layer for selective binding to the purified analyte molecules. Such detection layers, which are also designated as receptor layers, allow selective detection of analyte molecules and may be applied with today's coating technique in a wide spectrum of structural forms. In particular, the transverse sensitivity may be increased with such a detection device (or receptor device), since impurities still possibly present in the purified analyte material do not bind to the detection layer. In various embodiments, the receptor device may be formed by a module separated from the remaining component, which may be connected to the component before a measurement.

If the detection layer is structured in the form of an array and different layers are used, which each specifically bind other analyte molecules, multi-analyte detection method may also be achieved with the help of the system according to the invention.

According to a first embodiment of the present invention, the selectively bound analyte molecules are sensed optically with the help of fluorescence markers which are for example added to the analyte. This represents a widespread and therefore well established method for detecting selectively bound analyte molecules. Such an optical evaluation may be achieved by providing corresponding optics on the microfluidic component.

According to a further advantageous embodiment of the present invention, provision is made for detecting the selectively bound analyte molecules via an electrical route via charge effects. This has the advantage that no electro-optical transducers and no costly optics have to be provided and that an electrical output signal is directly present. Such an electrical detection may be based both on dielectric effects and on charges of the analyte and potentiometric or impedance analyzing methods may be applied. Together with corresponding electrochemical mediators, amperometric detection methods may also find application.

An example of an electric detection device, which detects the selectively bound analyte molecules via charge effects, is a biosensor on the basis of synthetic ion channels controlled by ligands. Such biosensors with the use of ligand-controlled ion channels (synthetic ligand gated ion channel, SLIC) are based on the principle that the permeability of ion channels in a lipid membrane is controlled by the specific binding of analyte molecules to the corresponding receptors.

The affinity reaction between the immobilized receptor and the analyte molecule binding to it, is therefore measured as a variation in the impedance of the total system, when a correspondingly equipped lipid layer on an electrode is immobilized. The lipid dual layer operates here both as an electrical insulation and as a blocking reagent in order to prevent unspecific adsorption. Since a flow of current can only take place by means of the ion channels, it is possible to perform extremely sensitive detection of binding events with such as sensor. The principle of such a sensor is for example indicated in Samuel Terrettaz et al.: "Highly Electrical Insulating Tethered Lipid Bilayers for Probing the Function of Ion Channel Proteins", Langmuir 2003, 19, 5567-5569, detection of proteins having been performed here.

Alternatively, mass-sensitive biosensors, for example quartz crystal microbalances, surface wave components or thin film resonators, may also be used for detecting the purified analyte.

Another possible detection method is the principle of Surface Plasmon Resonance (SPR). In an SPR system, transducers in the form of gold islands are provided as an integrated receptor unit, and an external detection unit measures the variations in the SPR angle as a function of the bound analyte molecules.

The present invention may be applied in a particularly advantageous way to the purification and detection of small nucleic acid molecules, in particular ribonucleic acid molecules. Especially for genomic identification of bacteria, tmRNA (transfer messenger ribonucleic acid), a bacterial RNA, which has both messenger and also transfer properties may be used.

TmRNA typically consists of relatively few nucleotides (<400) and has been identified in all sequenced bacterial species up to now (see W. Schonhuber et al.: "Utilization of tmRNA sequences for bacterial identification", BMC Microbiology, 2001, 1-20). Since tmRNA is a molecule amplified in a natural way (for example 1,000 copies per cell are available in *E. coli*), it is an interesting analyte for the genetic identification of bacteria. With the microfluidic purification according to the invention, it is possible to advantageously do away with using a polymerase chain reaction (PCR) for detection.

When using the integrated microfluidic component according to the invention for detecting bacterial tmRNA, the detection of the purified RNA takes place via a hybridization experiment. In the case of the SLIC-Biosensor, the respectively complementary oligonucleotide, a so-called "capture oligo" is immobilized on the ion channels and the hybridization event controls the permeability of the ion channels for available ions and thus influences the impedance of the sensor layout.

According to an advantageous enhancement of the present invention, the integrated microfluidic component comprises additional conditioning devices for treating the still not purified sample and/or for treating the purified analyte molecules. Thus the conditioning device may comprise for example a disruption device for disrupting the sample in the sample chamber. According to this embodiment, the bacterial cells may be directly entered into the sample chamber and be for example broken down by means of AC-thermoelectric lysis. Thus the integrated fluidic component may further comprise at least one integrated conditioning device for treating the sample and/or for treating the purified ribonucleic acid molecules. In one embodiment, the integrated fluidic the conditioning device comprises a disruption device for disrupting the sample in the sample chamber and can be operated in order to carry out cell lysis preferably electrical, thermal mechanical, ultrasound-assisted, osmotic, enzymatic and/or chemical cell lysis. The sample chamber may have at least one electrode for carrying out the cell lysis and said at least one electrode may be formed by electrodes with a coplanar structure. Certain embodiments provide for a disruption device of at least one electrode which comprises a plurality of electrodes and which can be positioned in different planes (for example, on an upper side and an underside of a substrate).

The lyzed cell mixture is then directly purified according to the invention by electrophoretic filtration. By the separation taking place directly after the cell disruption, there is, however, no time for damageable degradation of possibly available RNAse. Actually, the time factors for the principles according to the invention represent an essential parameter: the longer the elution time for example, the higher the yield, but also the lower is the purity of the analyte material.

For an efficient combination of lysis and electrophoretic purification, different procedures may be used. As the simplest alternative, the electrophoretic purification according to the invention may take place directly following the lysis step, or else a lysis of the cells may first take place in an electrophoretic field gradient, so that both processes run in parallel. Additionally, RNase-inhibiting enzymes and chemicals may be added in order to further optimize the process.

In the collecting chamber, the purified RNA may then be hybridized on a biosensor array and the hybridization event may be further processed as an electrical or optical output signal. But, of course, other alternative conditioning devices may also be provided, for example separation, filtration, washing and focusing steps, further transport steps, further concentration, sedimentation, adsorption or degradation, may be performed. These additional steps may either take place in the sample chamber or in the collecting chamber. In this way, the integrated microfluidic component may also be adapted to more complex biochemical detection routines. Furthermore, it is clear to one skilled in the art that principles of integrated real-time PCR may also be provided as conditioning.

Moreover, a so-called real time NASBA (Nucleic Acid Sequence Base Amplification) may be provided as an alternative to real time PCR, NASBA being an amplification technique, which takes place at constant temperature and is specific for RNA molecules. Equally like in PCR, NASBA may be directly monitored by using fluorescent marker molecules.

The present invention will be explained in more detail in the following with the help of the advantageous embodiments illustrated in the appended drawings. Similar or corresponding details of the object according to the invention are provided with the same reference symbols.

FIG. 4 shows a layout according to a second embodiment in a schematic illustration after filling the sample;

FIG. 5 shows the layout from FIG. 4 during the purification process;

FIG. 6 shows the layout from FIG. 4 during the detection process;

Figure 1:
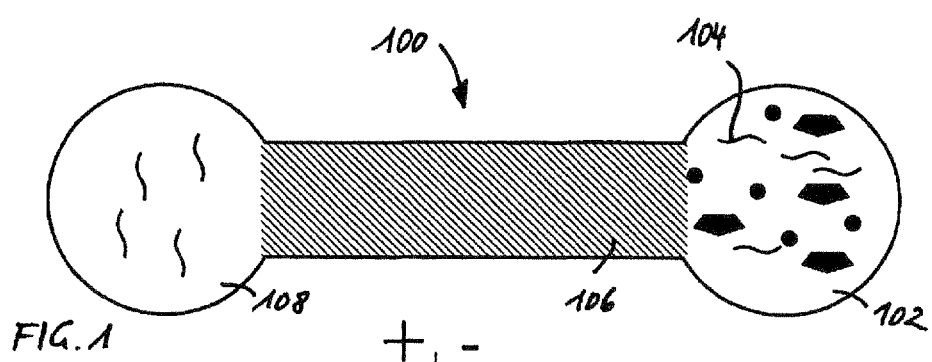
FIG. 1 shows a schematic illustration of a first embodiment of the integrated microfluidic component according to the invention in the initial state.
Figure 2:
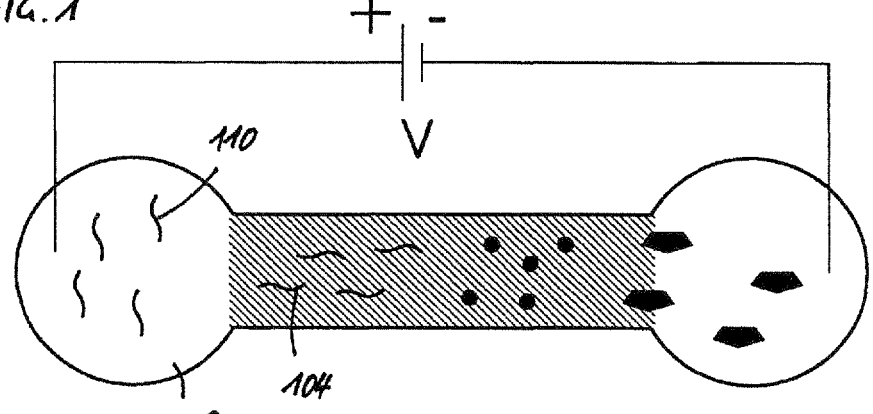
FIG. 2 shows the layout of FIG. 1 during a process for purifying the analyte molecules.
Figure 3:
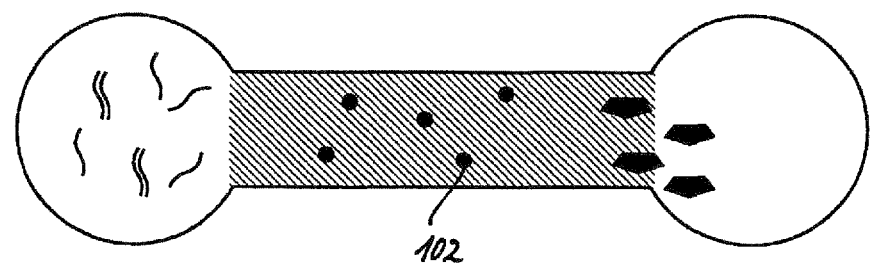
FIG. 3 shows the layout from FIG. 1 during a process for detecting the purified analyte molecules.

The structure and the mode of operation of the integrated microfluidic component 100 according to the invention are to be explained in detail in the following with reference to FIGS. 1-3. The microfluidic component 100 in its simplest embodiment comprises a sample chamber 102 for receiving a sample, which contains the analyte molecules 104. As for the sample molecules 104, these are, for example, RNA molecules such as for example tmRNA, which allow detection of bacteria. The microfluidic component further has a separation section 106 along which the sample moves and the analyte 104 is thereby separated from the remaining sample constituents. The sample may be a nucleic acid mixture, a cell lysate or else also a cell mixture.

The separation section 106 according to the present invention is formed by a gel filtration path, which has one or more electrophoresis gel matrices. After applying the voltage required for electrophoretic separation between the beginning and the end of the separation section 106, the analyte molecules to be purified move in the direction of a collecting chamber 108. In order to detect the purified RNA molecules, the complementary oligonucleotide 110 is immobilized in the collecting chamber as a detection layer. The electrophoresis voltage is then maintained until a sufficient amount of RNA has reached the collecting chamber 108 and is then switched off, so that the remaining larger sample constituents 112 do not attain the collecting chamber 108. Unspecific RNA fragments cannot bind to the receptor layer 110. The completed hybridization is then detected by means of fluorescence marking either optically or electrically, as this is illustrated more accurately in the following, by means of a biosensor based on ion channels controlled by ligands.

The integrated microfluidic component according to the invention may be a planar microchip such as it is for example produced by structuring a Pyrex glass wafer. The sample chamber and the collecting chamber may contain integrated phase guiding devices for controlled intake and issue of liquid according to P. Vulto et al.: "Selective sample recovery of DEP-separated cells and particles by phaseguide-controlled laminar flow", J. Micromech. Microeng. 16, 2006, 1847-1853.

Alternatively, the integrated microfluidic component may also have a three-dimensional arrangement. A vertical three-dimensional construction of an integrated analysis system provides quite a few essential advantages in comparison with a planar configuration: a larger surface-to-volume ratio may be produced. This is advantageous, in order to increase the contact surface area between the gel and the sample solution, since larger surfaces reduce the risk of aggregates. Further, a larger amount of initial sample liquid may be applied, which is concentrated by electrophoretic purification to a microliter volume. Gels and layers from a plurality of gels may, in the case of a 3D layout, simply be prepared by pouring. A vertical setup additionally enables a modular concept, in which the inexpensive and simple sample preconditioning elements may be prepared separately from the sensitive biosensor or affinity sensor elements. Both parts are connected together shortly before a measurement is conducted.

Finally, gravity may be utilized for a three-dimensional layout as a motor for fluidic actuation or sedimentation.

The simplest layout described up to now for the integrated purification and hybridization of tmRNA may, as shown in FIGS. 4-6, be extended to different additional steps. The component designated with the letter "f" then symbolizes one or more conditioning steps, such as for example a lysis, a separation, a filtration, a washing step, a focusing, a transport step, a concentration, a sedimentation, an adsorption or a degradation step. Such additional steps may be performed both inside the sample chamber 102 and inside the collecting chamber 108.

For example, a cell sample may be introduced into the sample chamber; in a subsequent conditioning step, the cells are lyzed via electrical, chemical, thermal, osmotic or mechanical routes, in order to release RNA. In the next step, the released RNA is purified along the electrophoresis section, as shown in the previous figures. In the collecting chamber 108, RNA hybridizes with the immobilized receptor molecules, which are applied for example as an array on a substrate. Detection of the hybridized molecules takes place either via fluorescence marking or via electrical or mass-sensitive routes.

Since the lysis and purification take place in one and the same integrated microfluidic system, the time during which the sensitive RNA is exposed to disintegrating RNase molecules, is reduced to a minimum and RNA degradation may thereby be prevented.

A still more complex procedure might include that the analyte cells are first released by means of dielectrophoresis of other cells and of the cell supernatant and only then an electrical or chemical cell lysis occurs. Next, large proteins may be removed from the sample mixture, for example by means of selective adsorption followed by sedimentation, before performing the actual electrophoresis step along the gel path. After collection in the collecting chamber 108, a real time PCR may be conducted in which the sample is distributed over several PCR wells and an affinity reaction, amplification and fluorescence detection are carried out.

Moreover, it is basically clear to a person skilled in the art, that of course not only a single separation section, but several of them may be provided, which open out for example in a plurality of collecting chambers and allow analysis on several analytes inside the same sample. Alternatively or additionally, a plurality of sample chambers may also be provided, in order to be able to simultaneously analyze various samples. Further, every type of small RNA, DNA, peptides or proteins, may be considered as analyte molecules.

Figure 7:
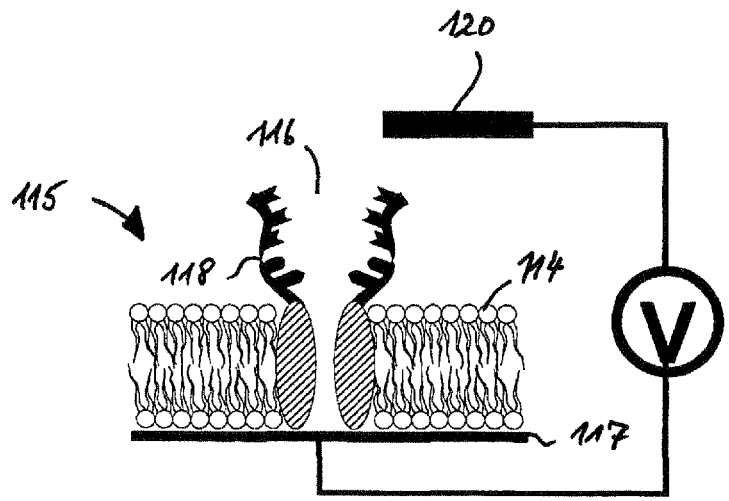
FIG. 7 shows a schematic illustration of a receptor unit for selective binding of the purified analyte molecules based on synthetic ligand-controlled ion channels before the hybridization process.
Figure 8:
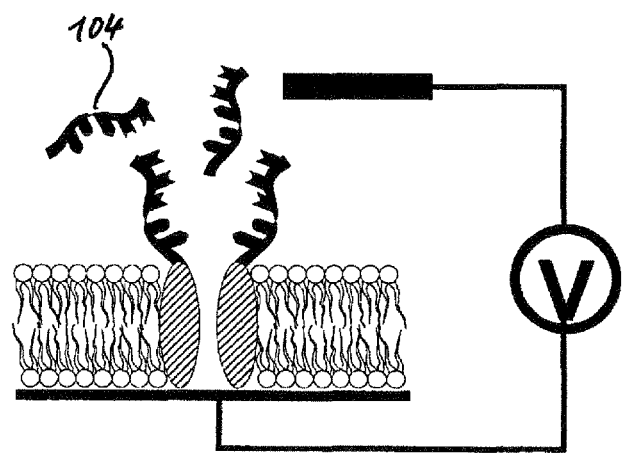
FIG. 8 shows the layout of FIG. 7 during the binding of the purified RNA molecules.
Figure 9:
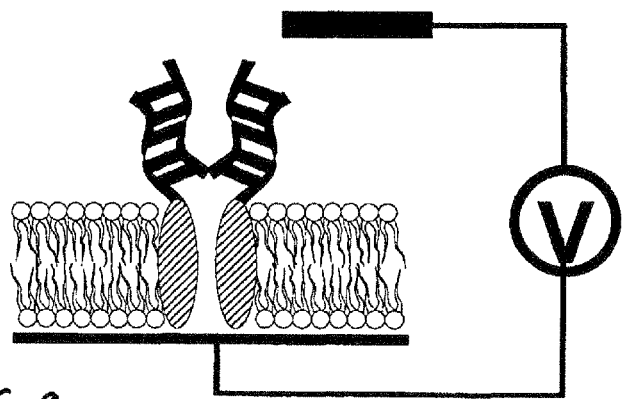
FIG. 9 shows the layout of FIG. 7 after binding the purified RNA molecules.
Figure 10:
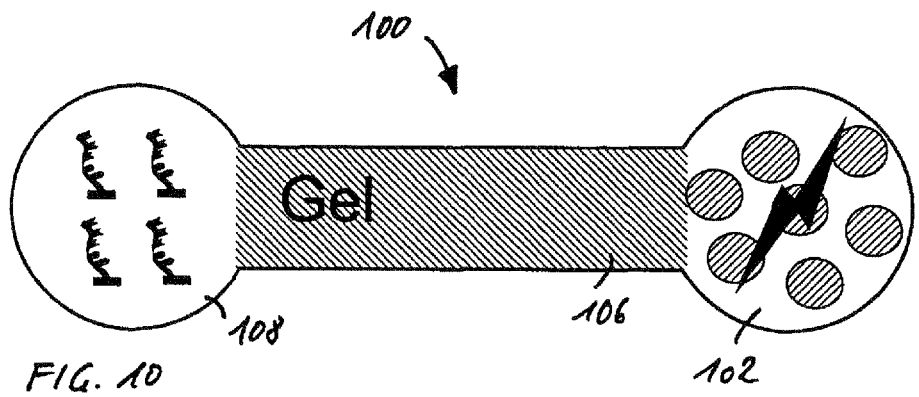
FIG. 10 shows a schematic illustration of a further advantageous embodiment of the integrated microfluidic component according to the invention.
Figure 11:
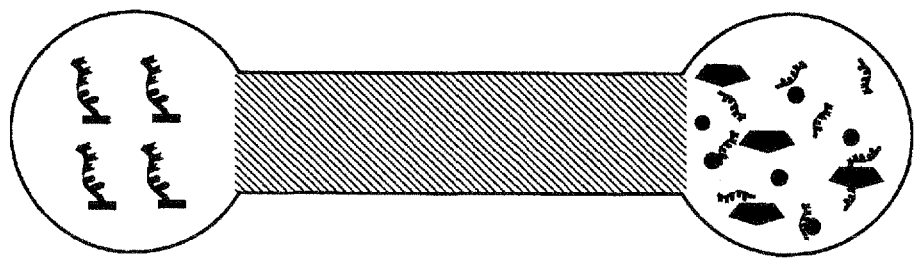
FIG. 11 shows the layout of FIG. 10 after disruption of the sample.
Figure 12:
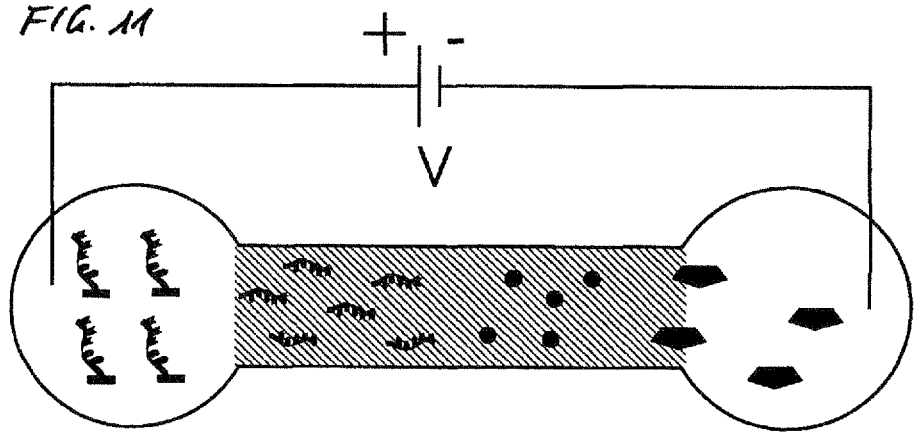
FIG. 12 shows the layout of FIG. 10 during the electrophoretic separation.
Figure 13:
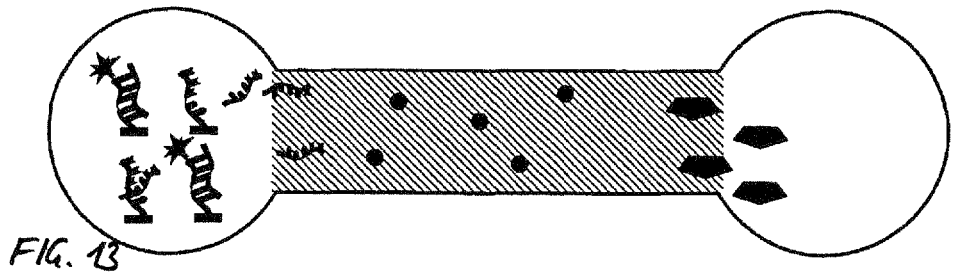
FIG. 13 shows the layout of FIG. 10 during the detection process.

With reference to FIGS. 7-9, a possible embodiment of a biosensor for detecting tmRNA molecules in the collecting chamber is to be explained in the following.

In this case, the applied biosensor 115 is based on the principle of the synthetic ligand-controlled ion channel (synthetic ligand gated ion channel, SLIC). Such a SLIC biosensor 115 comprises a lipid dual layer 114, in which the ion channels 116 bear capture oligonucleotides 118 as receptors controlling permeability. For example, the impedance between the substrate 117 and a counter-electrode 120 is evaluated as a measurement signal. If the tmRNA 104 to be detected binds to the complementary oligonucleotides selectively, the ionic permeability of the channels 116 changes and therefore, the measurable impedance changes also.

Since an electric current only flows through the ion channels 116, with the layout according to the invention, it is possible to obtain an extraordinarily accurate detection of the hybridization events.

A possible embodiment of the integrated microfluidic component 100 using an affinity array, for example a SLIC biosensor, is sketched in FIGS. 10-13. First, a cell lysis of the entire cells 122 to be analyzed is performed here in the sample chamber 102. Then, the analyte molecules to be detected, for example RNA, in particular tmRNA components 104, are separated along the separation section 106 from the remaining cell constituents and hybridized with immobilized receptor molecules in the sample chamber. The binding event leads to a change in the impedance of the SLIC sensor and may be measured as an electric output signal.

However, the electrophoretic separation section 106 does not have to necessarily consist of only a homogenous and symmetric gel. It is possible to also use several gels, which for example vary in pore size, in gel material or in buffer composition. The gels may be provided in various forms and in various electrode configurations, which are used for the actuation.

Figure 14:
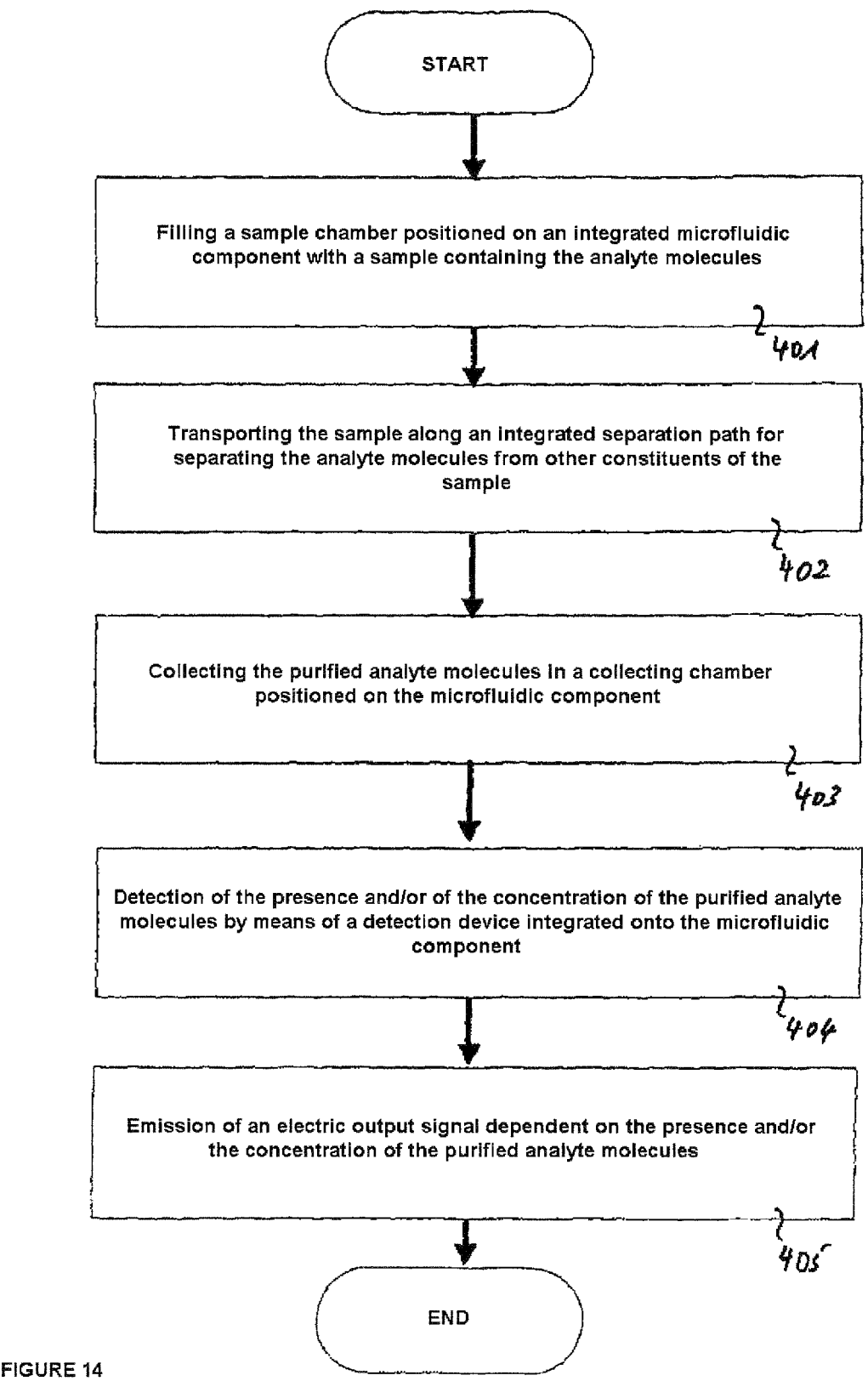
FIG. 14 shows a flow chart of the purification and detection process.

The operating mode of the layout shown in FIGS. 10-13 is summarized as a flow chart in a general view in FIG. 14. The detection method begins with the filling of one sample chamber positioned on the integrated microfluidic component with a sample containing the analyte molecules (step 401). By applying a suitable voltage along the integrated separation section, for separating the analyte molecules from the other components of the sample, the sample is transported in step 402. The purified analyte molecules gather in a collecting chamber also positioned on the microfluidic component (step 403). Next, the presence and/or the concentration of the purified analyte molecules may be detected by means of an integrated detection device also on the microfluidic component (step 404). Finally in step 405, an electric output signal which depends on the presence and/or the concentration of the purified analyte molecules is emitted, this signal being accessible to further signal processing.

Figure 15:
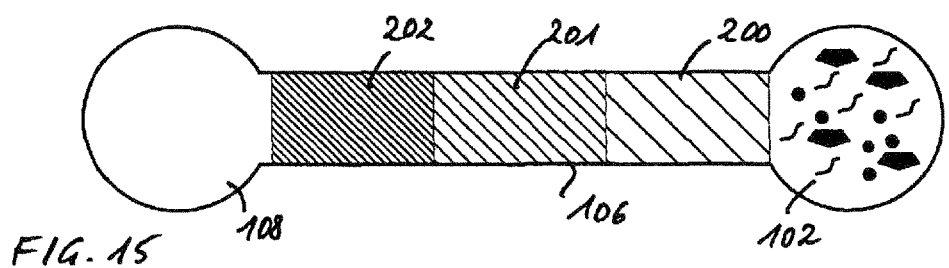
FIG. 15 shows a schematic illustration of a further advantageous embodiment of the integrated microfluidic component according to the invention, in which the separation sections have several gels with different pore sizes.
Figure 16:
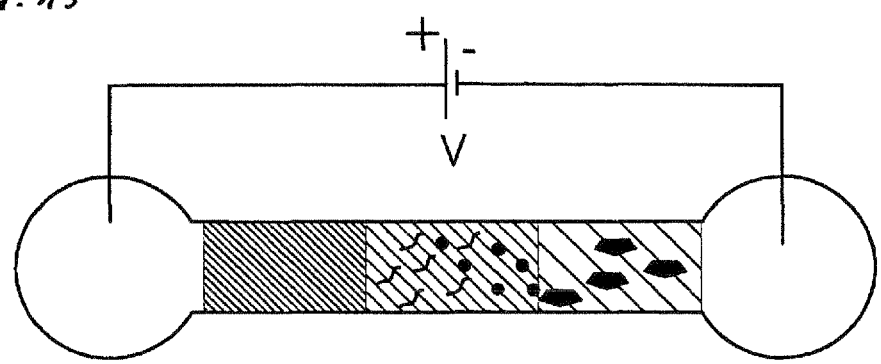
FIG. 16 shows the layout of FIG. 15 during the purification process.
Figure 17:
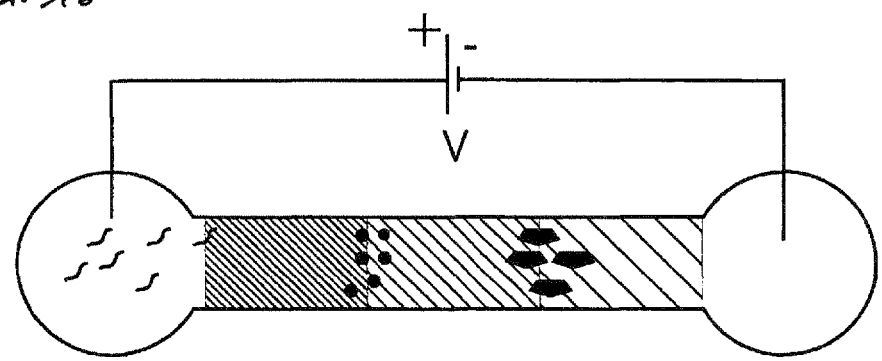
FIG. 17 shows the layout from FIG. 15 after a completed purification process.
Figure 24:
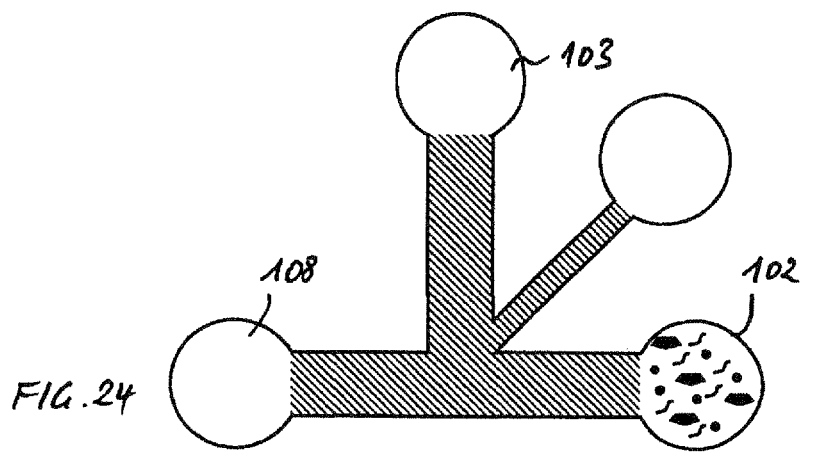
FIG. 24 shows a schematic illustration of a refined layout according to FIG. 21 with an additional waste chamber.
Figure 25:
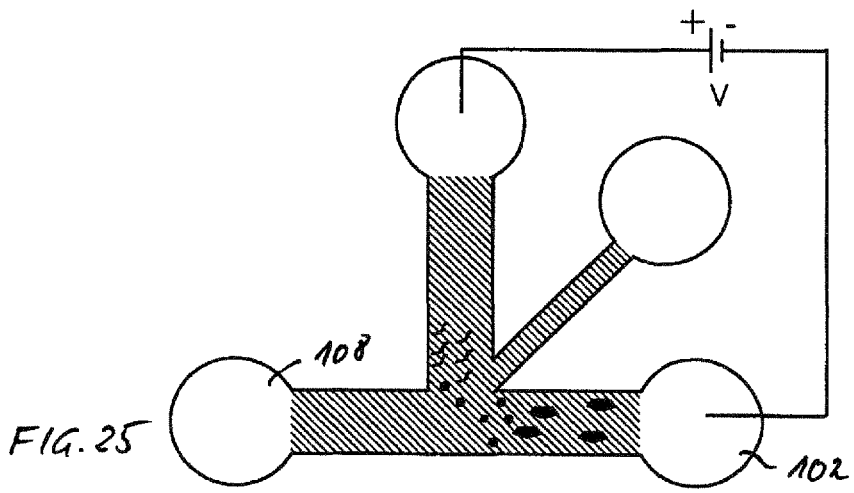
FIG. 25 shows the layout from FIG. 24 during a first separation step.
Figure 26:
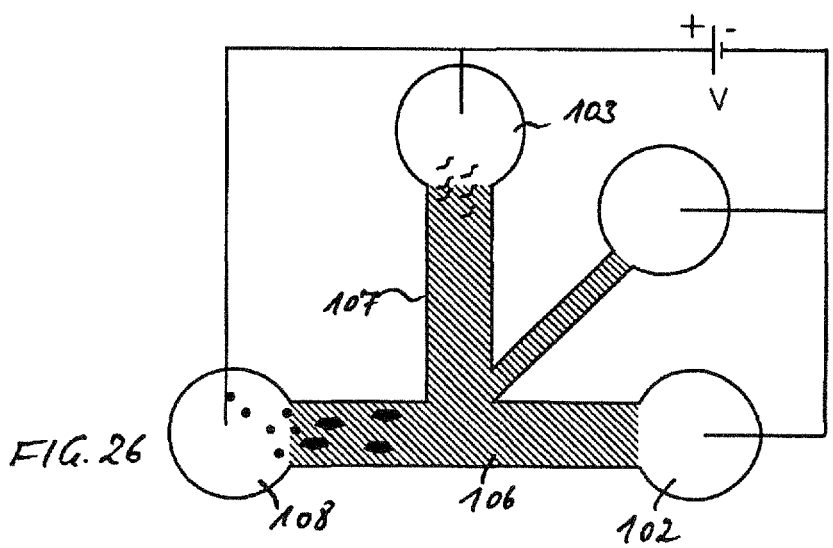
FIG. 26 shows the layout from FIG. 24 during a second separation step.
Figure 27:
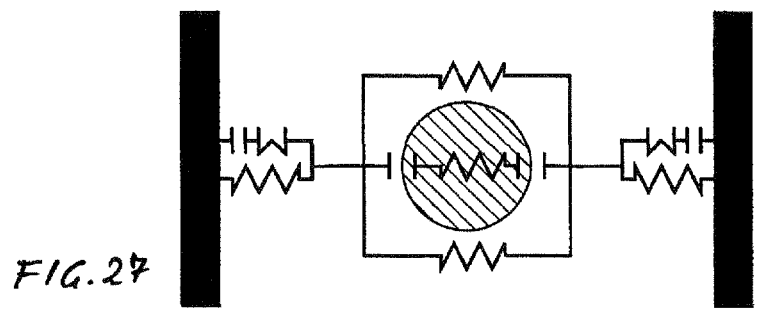
FIG. 27 shows an electrical replacement circuit diagram for the sample chamber during the electrical cell lysis.
Figure 28:
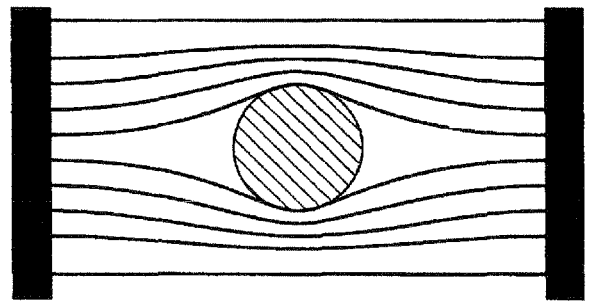
FIG. 28 shows a schematic illustration of the current path upon applying a DC voltage.
Figure 29:
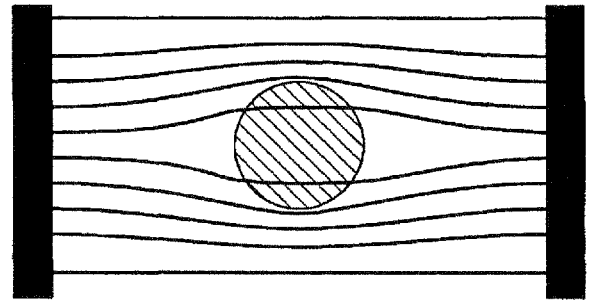
FIG. 29 shows a schematic illustration of the current path for alternating voltages, when the buffer is more conductive than the cell cytoplasm or when too low frequencies are selected.

With reference to FIGS. 15-17, a first example is to be described in which the separation section 106 is formed by a gradient of gels which vary in density. As this is apparent from this illustration, the separation section 106 consists of three different gels, it being clear for a person skilled in the art that their number is only selected exemplarily. The first gel 200 has a larger pore size, so that in a first step, large impurities are separated from the sample. The successive gels 201, 202 each have a decreasing pore size and their sieving effect increases. Mechanisms as shown in FIGS. 24-26, may for example prevent overloading of the gel or cause concentration of the sample material before the separation.

Figure 18:
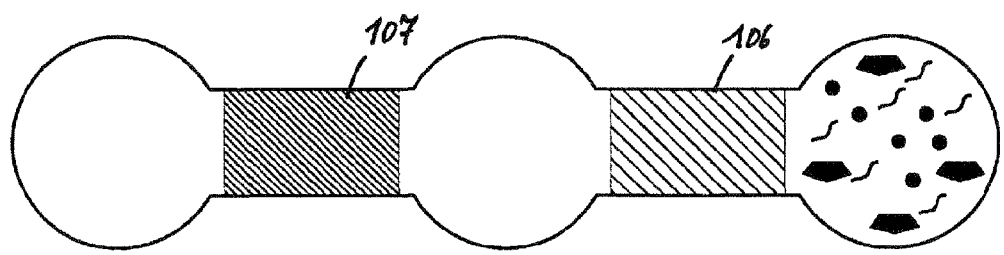
FIG. 18 shows a schematic illustration of a further advantageous embodiment of the integrated microfluidic component according to the invention with multiple gel filtration sections.
Figure 19:
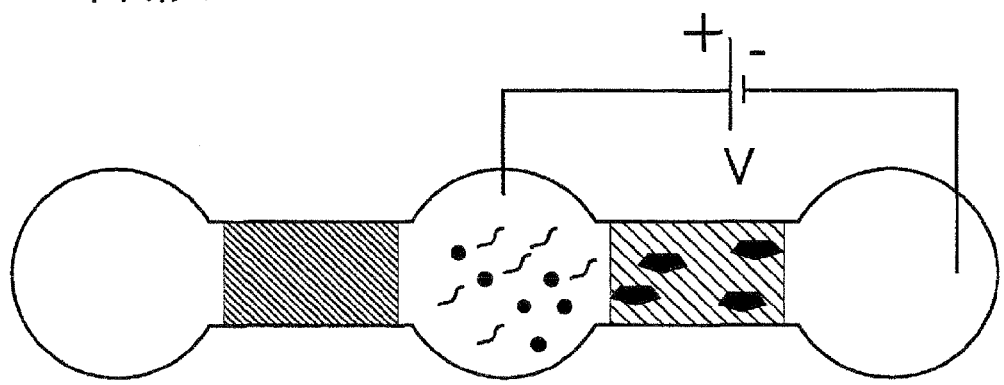
FIG. 19 shows the layout from FIG. 18 upon applying a voltage on a first gel filtration section.
Figure 20:
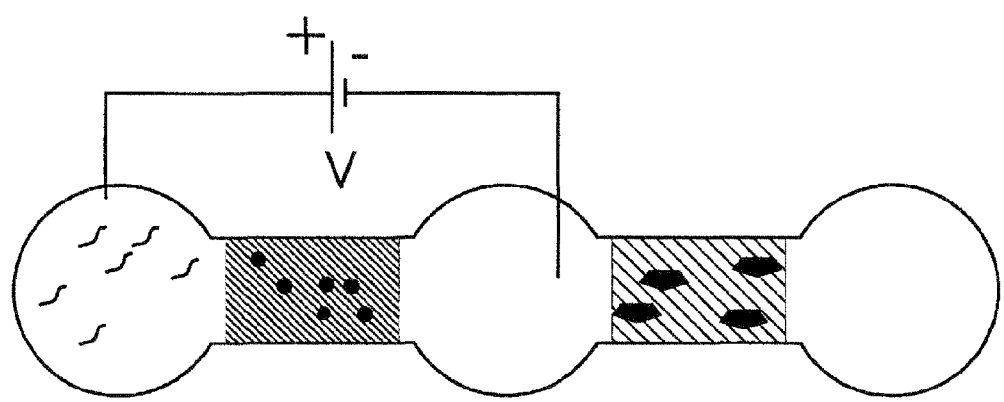
FIG. 20 shows the layout from FIG. 18 upon applying a voltage on a second gel filtration section.

A further example for multiple gel separation sections is shown in FIGS. 18-20. Here several gel sections 106, 107 and collecting chambers in succession are connected in series. Of course, the number of serially successive steps may be arbitrarily adapted to the requirements. In the embodiment shown, two gel separation sections are connected as a cascade. After each separation step, the sample is collected in a collecting chamber. The layout shown here has the advantage that it delivers higher purity of the finally extracted analytes as well as a larger amount of analyte material. The plurality of separation sections 106, 107 may be actuated either independently of each other as shown in FIGS. 18-20, or else by the same electrodes. Further, the gel separation sections 106, 107 may have identical properties or else different properties as regards pore size, material or buffer composition.

Hitherto it was always assumed that the analyte molecules have the fastest migration properties as compared with the remaining sample constituents. However, this does not have to be always necessarily the case. It is quite possible that various sample constituents also have faster electrophoretic migration properties than the analyte material to be purified. This equally undesirable material may be removed advantageously by deviating the sample into a side channel. This procedure is sketched in FIGS. 21-23 as well as 24-26.

Figure 21:
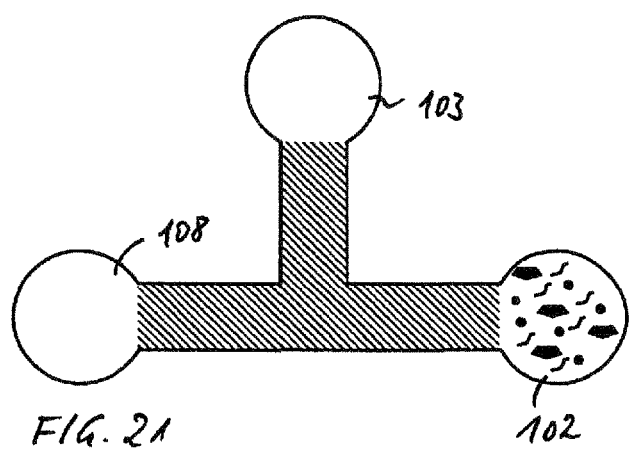
FIG. 21 shows a schematic illustration of a further advantageous embodiment, which has a side channel for preliminary separation of faster species.
Figure 22:
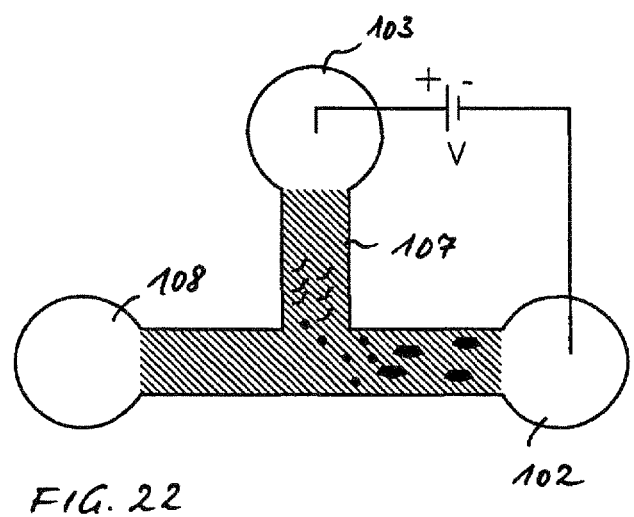
FIG. 22 shows the layout from FIG. 21 upon applying a voltage between the sample chamber and a first collecting chamber.
Figure 23:
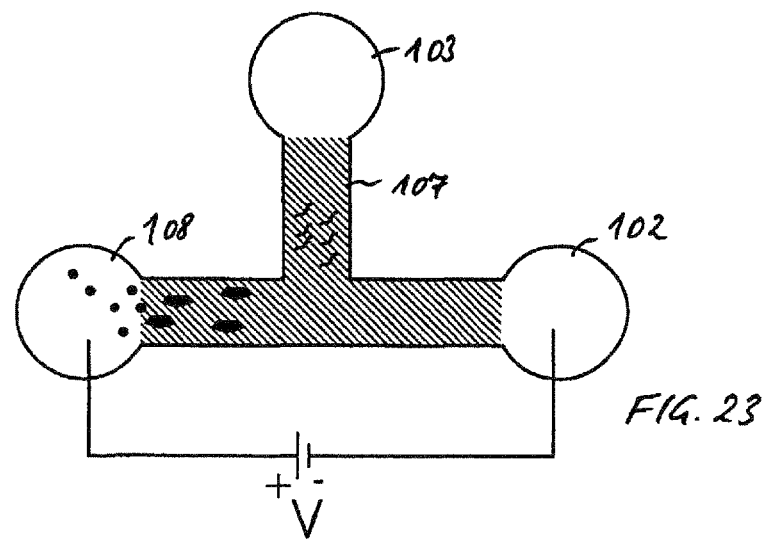
FIG. 23 shows the layout from FIG. 21 upon applying a voltage between the sample chamber and a second collecting chamber.

As illustrated in FIGS. 21-23, the electrophoretic potential is then applied first between the sample chamber 102 and a side channel 107, until the fast migrating components have all entered the side channel 107. Then, as shown in FIG. 23, the potential is applied between the collecting chamber 108 and the sample chamber until the analyte material exists in a purified form in the sample chamber 108.

FIGS. 24-26 show a more complex layout in which a second potential is applied between an additional channel and the sample chamber on one side and the collecting chamber and the first channel on the other side. The pre-separated product may thereby be prevented from migrating back into the direction of the collecting chamber. Instead of this, it will migrate in the direction of the waste chamber 103.

Figure 30:
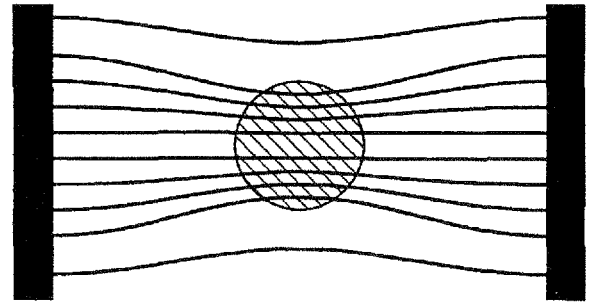
FIG. 30 shows a schematic illustration of the current path for alternating voltages, when the medium has lower conductivity than the cell cytoplasm.

In order to enable efficient cell lysis, an alternating current may be used which heats the sample. This process is schematically illustrated in FIGS. 27-30. The reference symbol 122 designates the cells to be disrupted. When the buffer, in which the cells 122 are dissolved, has lower conductivity than the cytoplasm of the cells, the current flow density will be highest inside the cells, as this is shown in FIG. 30. This means that the volume-dependent production of heat is highest inside the cells, so that the cells are calorifically disrupted, without having to heat up too much the environment around the cells. This method is particularly effective for cells with thick cell membranes such as, for example, Gram-positive bacteria. Additionally, various lysis reagents may be added to the sample solution. This electrothermal lysis in a miniaturized configuration is known, for example, from J. West et al.: "Accessing DNA by low voltage alternating current Joule effect heating", Analytica Chimica Acta 527 (2004) 1-12. In contrast to the present invention, the buffer conditions are, however, not adapted therein to the respective cell conductivities, in order to obtain a high current density inside the cells. Further, in this known solution, no purification steps according to the present invention are provided.

The approach of locally heating cells with a lower buffer conductivity as compared with cytoplasm conductivity, is in particular advantageous in a microsystem, since a lysis may be performed by heating in this way, without bringing the sample liquid to a boil so that gas bubble formation may be prevented. Furthermore, the sample solution may be used for cooling the lysis products directly after the lysis step, so as to be able to prevent fast RNA degradation. The combination of local cell heating with an additional sample cooling, for example, by means of Peltier elements allows an optimized combination of thermal cell lysis and buffer cooling.

According to a further advantageous embodiment, the sample may additionally be dissolved in a buffer, which represents at the same time a separation matrix. For example, liquid polymeric solutions as they are applied for capillary electrophoresis may also be provided in the present integrated layout. Such liquid separation matrices may be used in order to directly carry out a first separation of very large and smaller sample constituents, in order not to overload the gel or not to block the current path by aggregation of too much material in one place. At the same time, such polymeric solutions may also be used as an additive to the lysis buffer with low conductibility.

As is generally known, electrophoresis is an effect which depends on the intensity of the electric field. This field intensity is influenced i.a. by the applied potential (or the current) and the geometry of the microstructure, through which this current flows. The electric resistance of a microchannel depends linearly on the ratio between its length and the cross-sectional surface area. A locally increased cross-sectional surface area, i.e. an increased channel width or height, leads to a lower local field intensity.

Since the electrophoretic mobility of the different species depends non-linearly on the electrophoretic field intensity, as this is known for example from J. Viovy: "Electrophoresis of DNA and other polyelectrolytes: physical mechanisms", Rev. Modern Physics, Vol. 72, No. 3, 2000, 813-872, such a principle may be used in order to thereby manipulate the electrophoretic separation. A widening of the collecting chambers after gel purification may, for example, be used in order to slow down the migration rate of the species and thus to prevent them from actually reaching the actuation electrode.

The actuation electrodes for the electrophoretic separation may either be integrated into the microstructure or be formed as external electrodes. The advantage of integrated electrodes in a closed chamber lies in that the sample volume is exactly defined by the chamber and electrode geometry. Integrated electrodes in a closed microchannel further prevent evaporation of the sample liquid. A further advantage of integrated electrodes is that they are disposed of after use and do not have to be used again.

A drawback of electrodes in a closed space is, however, the fact that hydrolysis takes place on the electrode surfaces, oxygen being formed at the positive electrode and hydrogen at the negative electrode. This gas formation may interrupt the current path between both electrodes and therefore prevent electrophoresis. Non-modified electrodes therefore only allow a limited electrophoresis time.

This problem can only be overcome by modifying the electrodes in order to let, for example, different electrochemical reactions occur on the electrodes, or by positioning the electrodes in an open air space so that the gas may escape, or by providing a gas storage space which further leads to the gas moving in a direction in which it does not interfere with the path of the current.

With reference to FIGS. 31-34, 35-37 as well as 38-40, various electrode shapes are proposed.

Figure 31:
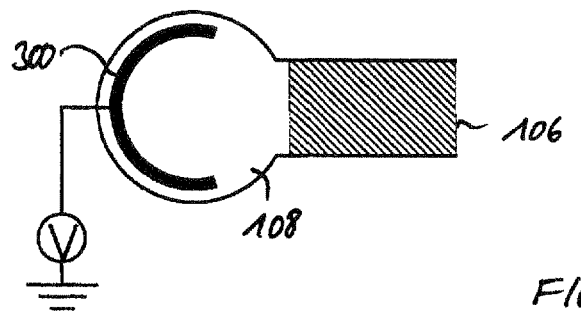
FIG. 31 shows a schematic illustration of a first electrode configuration in a closed microchamber.
Figure 32:
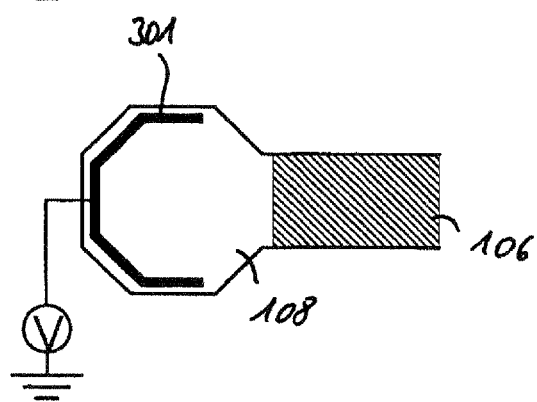
FIG. 32 shows a second electrode configuration for a closed microchamber.
Figure 33:
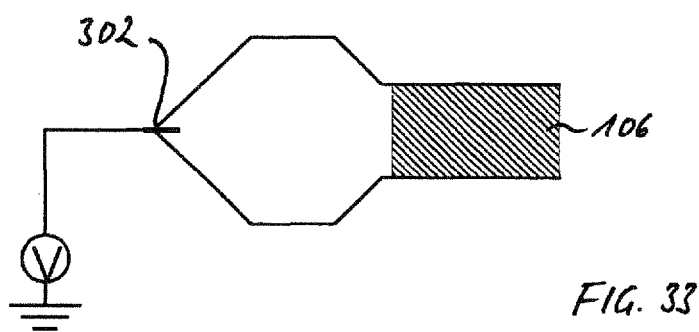
FIG. 33 shows a third electrode configuration for a closed microchamber.
Figure 34:
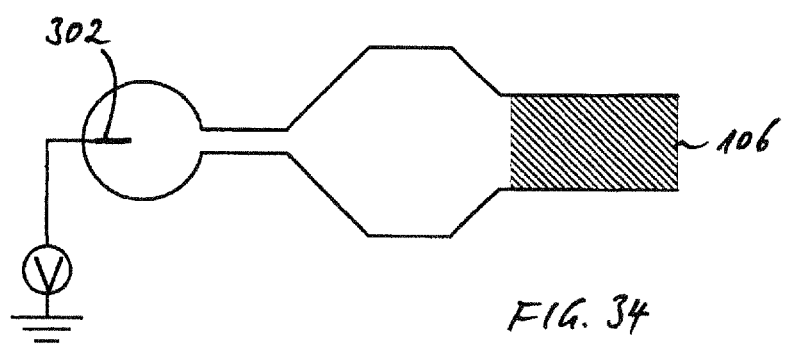
FIG. 34 shows another electrode geometry for a closed microchamber.

FIGS. 31-34 show various integrated electrodes in a closed microchamber. The electrodes shown in FIGS. 31 and 32 are positioned on the periphery of the collecting chamber 108, so that they delimit the collecting chamber 108 with their shape. Each point of the electrode 300 should be structured in such a way that it is approximately equidistant from the outlet of the gel separation path, in order to guarantee homogeneous filling of the collecting chamber. Analogously, this applies to the sample chamber, for which it is desirable that a homogenous electric field occurs over the entire sample. In FIGS. 33 and 34, point electrodes 302 are sketched.

For example, the electrode 302 may be housed in an additional electrode chamber (as seen in FIG. 34) or positioned on an outermost end of the collecting chamber 108. The configuration of FIG. 33 may also be achieved in a configuration in which an external open electrode is provided.

Figure 35:
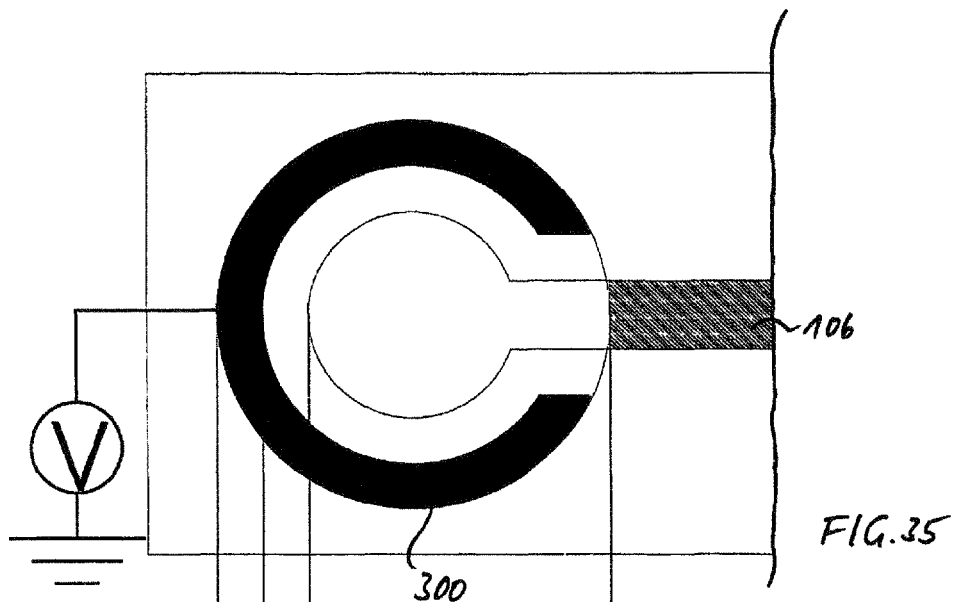
FIG. 35 is a top view of an open integrated electrode layout.
Figure 36:
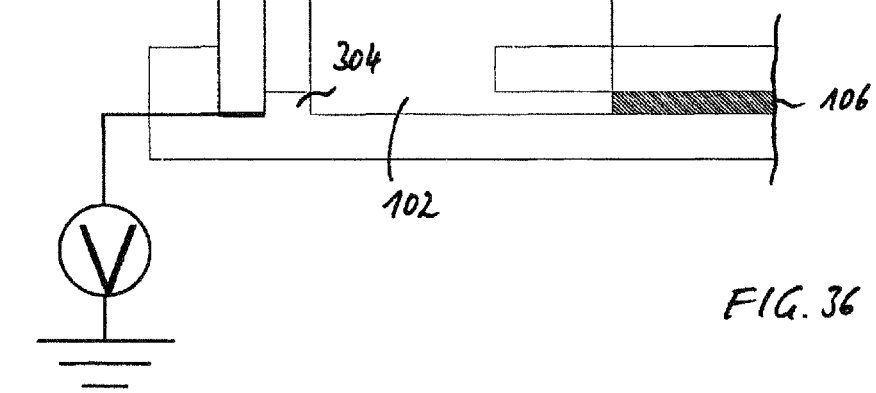
FIG. 36 shows a sectional representation of the layout from FIG. 35.
Figure 37:
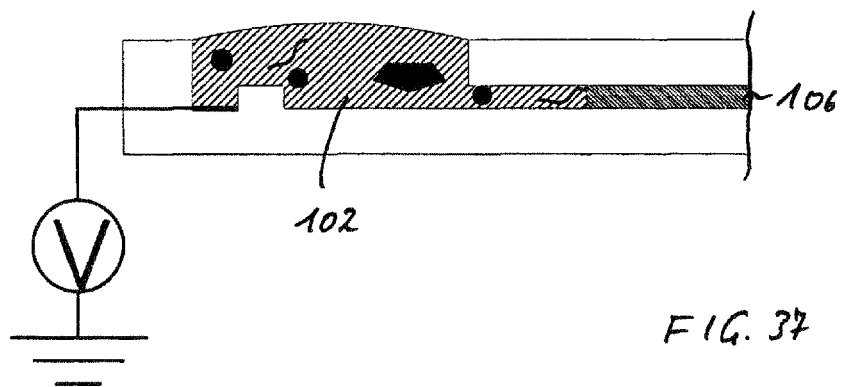
FIG. 37 shows the layout from FIG. 36 in the filled state.

Such an open electrode is illustrated in FIGS. 35-37. Here, the electrode 300 is exposed to open air, in order not to be hampered by gas formation. In this indicated embodiment, the electrodes are formed in the sample chamber. The sample chamber 102 further contains an electrically insulating barrier 304, which additionally forces the current to flow through the sample, before entering the gel separation path. The sample is introduced here as a droplet from the outside.

Figure 38:
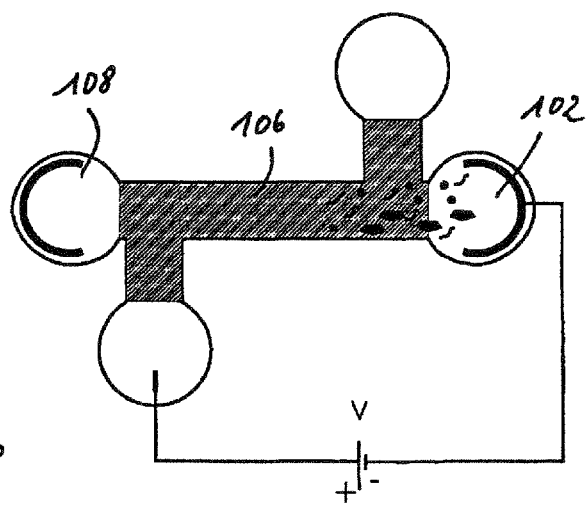
FIG. 38 shows a schematic illustration of a further advantageous embodiment of the integrated microfluidic component according to the invention.
Figure 39:
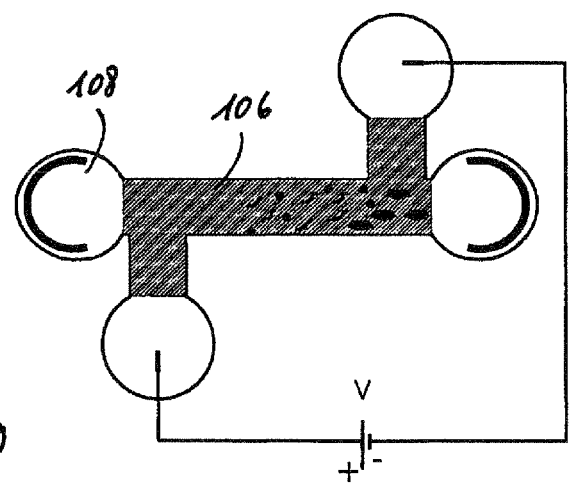
FIG. 39 shows a schematic illustration of a further advantageous embodiment.
Figure 40:
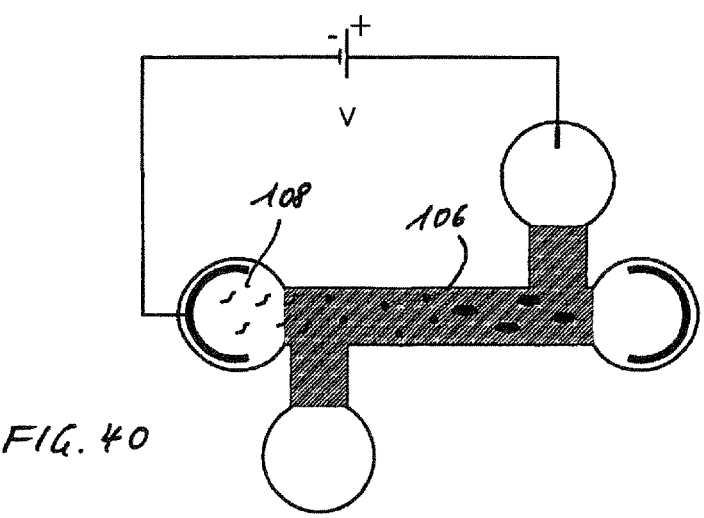
FIG. 40 shows a schematic illustration of another advantageous embodiment.
Figure 41:
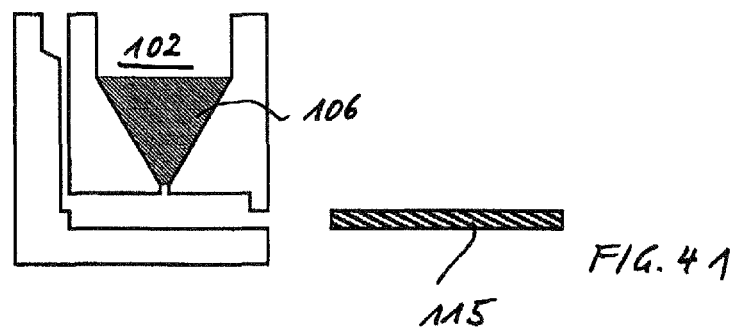
FIG. 41 shows a section through a three-dimensional embodiment of the microfluidic component according to the invention during the assembly.
Figure 42:
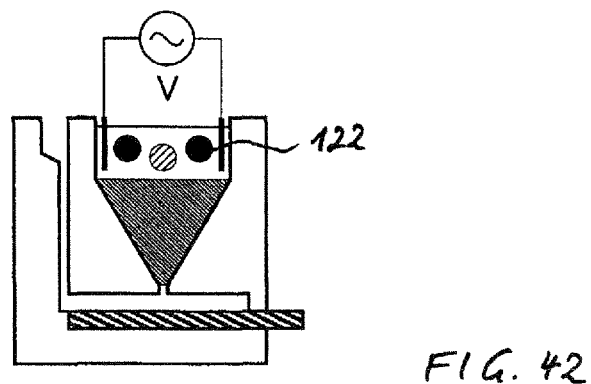
FIG. 42 shows the layout from FIG. 41 in the assembled condition during a cell lysis process.

As sketched in FIGS. 38-40, integrated and open electrodes may, however, be combined together. In the embodiment shown here, a first migration of the sample into the gel is induced by actuation of the electrode of the sample chamber together with an open electrode in a side channel. When the sample has completely entered the gel, separation occurs by actuation of the open electrodes (FIG. 39). Elution of the purified analytes finally occurs by actuation of the integrated electrode in an elution chamber and of an open electrode in a remote position of the separation channel. The embodiment shown here has the advantage that the separation times are not hampered by gas formation on the electrodes. Evaporation is not a problem here, since the open electrodes may be rinsed with buffer, without thereby influencing the purification process.

Further, modified electrodes may be used in a closed chamber. The electrodes should then be modified in such a way that a hydrolysis is replaced by an alternative electrochemical reaction. For example, the negative electrode may be formed out of silver chloride, so that during the actuation process the silver chloride is converted into silver, thereby forming chloride ions. With such a layout, production of hydrogen may be prevented on the negative electrode. Other materials, which may be used for the negative electrode, are silver iodide, silver bromide, zinc sulfate and copper sulfate. Also palladium, which is known to be able to store hydrogen on its surface, may be used for the negative electrode in order to prevent gas formation.

For the positive electrode, silver may be used, for example, which then dissolves into one of the aforementioned materials according to the prevailing buffer conditions. In this way, production of oxygen on the positive electrode may be prevented.

As already mentioned, a three-dimensional system with a vertical component has a number of significant advantages as compared with exclusively horizontal flat systems. The ratio of the gel surface area over the sample volume may be slightly increased and additionally, it is possible to achieve a very simple implementation of a modular system, in which the sensitive affinity component is produced separately from the simple pretreatment system.

Figure 43:
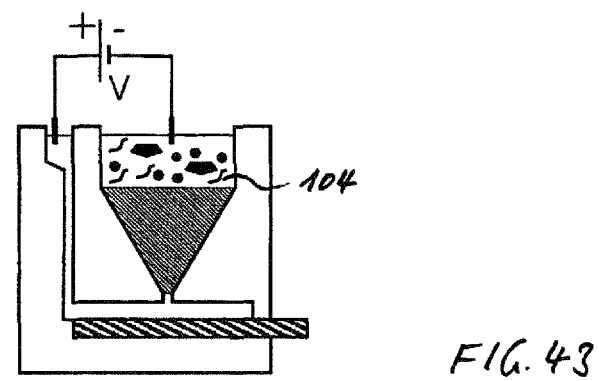
FIG. 43 shows the layout of FIG. 42 at the beginning of an electrophoresis process.
Figure 44:
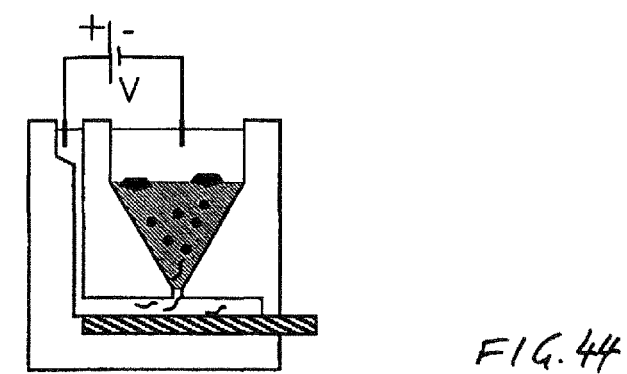
FIG. 44 shows the layout from FIG. 42 toward the end of an electrophoretic separation process.

An example of such a modular three-dimensional configuration according to the principles of the present invention is shown in FIGS. 41-44. According to this embodiment, the separation gel has a conical form. Preparing multiple gel separation sections may quite simply be achieved by a layered separation of various gel layers. The affinity chip 115 is inserted from the side and thus closes the microfluidic space. In the embodiment shown, outer open electrodes are used for the actuation. Depending on the cell disruption method, additional electrodes may further be provided for cell disruption. Disruption of the cells is shown here in FIG. 42, while FIGS. 43 and 44 show the electrophoresis process.

Figure 45:
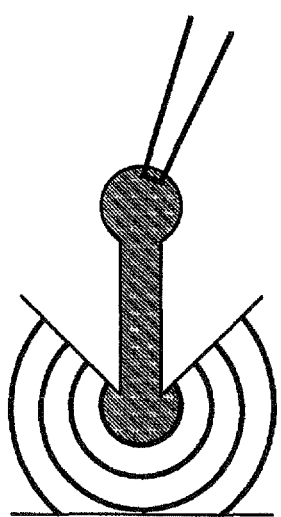
FIG. 45 shows a schematic illustration of the process for preparing a gel structure at a first instant of time.
Figure 46:
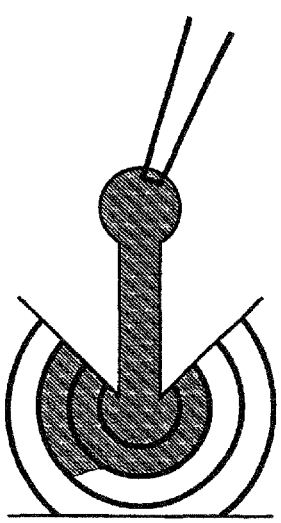
FIG. 46 shows a schematic illustration of the process for preparing a gel structure at a later instant of time.
Figure 47:
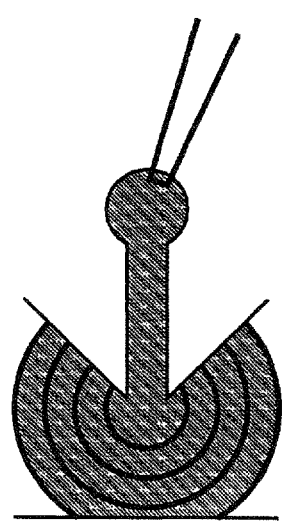
FIG. 47 shows the completed gel structure of FIGS. 45 and 46.

With reference to FIGS. 45-47, a possible preparation method for the gel separation sections is to be described subsequently. The gel may be incorporated into a microsystem by means of manual injection or with the help of a pump or a microdosage system. Typically, this takes place with the use of a pipette. In order to prepare a gel with a reproducible structure, so-called "phase guides" may be used. Phase guides are thin strips of a material, which locally changes the capillary forces in a fluidic system and therefore builds pressure barriers.

FIGS. 45-47 show a gel structuration with the help of phase guides, in which the gel is incorporated with a pipette. The phase guides control the progression of the gel front, so that the gel may be introduced into a reproducible structure.

With the help of the integrated microfluidic configuration according to the invention, it is therefore possible to perform highly sensitive, automated and miniaturized purification and detection of analyte molecules. In particular in connection with tmRNA molecules, it is therefore possible to achieve detection of bacterial species without using PCR steps. Sample conditioning and affinity detection may be carried out in an integrated form inside a closed microfluidic component.

Furthermore, the described combined analysis procedure which uses cell lysis, electrophoretic gel purification followed by a hybridization experiment, is a novel approach, not only on a microfluidic level, but also as a macrobiological procedure.

The invention claimed is:

1. An integrated fluidic component for purification of nucleic acid molecules, wherein the component comprises:
    at least one sample chamber for receiving a sample containing the nucleic acid molecules, the sample being a cell lysate or cell mixture;
    at least one electrophoretic gel separation section for separating the nucleic acid molecules from other components of the sample;
    at least one collecting chamber for receiving the purified nucleic acid molecules, wherein the collecting chamber has at least one integrated receptor device for detecting the presence and/or the concentration of the purified nucleic acid molecule; and
    an optional side channel for incorporating the gel into the electrophoretic gel separation section, wherein the electrophoretic gel separation section is directly connected with the sample chamber, so that the sample is purified directly through the electrophoretic separation section, wherein the gel separation section is adapted so as to separate ribonucleic acid molecules from the sample and the electrophoretic gel separation section comprises phase guides creating local changes of capillary forces for controlling the progression and reproducible shaping of the gel front during gel incorporation into the electrophoretic gel separation section, wherein the phase guides comprise thin strips which locally change the capillary forces into the electrophoretic gel separation section and create pressure barriers which control the gel spatially within the gel separation section.

2. The integrated fluidic component according to claim 1, wherein the receptor device comprises a structured detection layer as an array for selectively binding the purified ribonucleic acid molecules.

3. The integrated fluidic component according to claim 1, wherein the receptor device detects selectively bound ribonucleic acid molecules by means of an optical readout of a fluorescence signal.

4. The integrated fluidic component according to claim 1, wherein the receptor device electrically detects selectively bound ribonucleic acid molecules via a charge effect selected from impedance spectroscopy, potentiometry or amperometry.

5. The integrated fluidic component according to claim 4, wherein the receptor device comprises a biosensor based on synthetic ligand-controlled ion channels.

6. The integrated fluidic component according to claim 1, wherein the receptor device detects selectively bound ribonucleic acid molecules by means of surface plasmon resonance.

7. The integrated fluidic component according to claim 1, wherein the electrophoretic gel separation section is formed by a sequence of different gels or a gradient of gels.

8. The integrated fluidic component according to claim 7, wherein different parts of the sequence of gels may be actuated independently of each other by electrodes which are integrated into the electrophoretic gel separation section.

9. The integrated fluidic component according to claim 8, wherein the electrophoretic gel separation section has at least one further side channel, which may be actuated by at least one additional electrode.

10. The integrated fluidic component according to claim 9, wherein said at least one further side channel is for a pre-separation and collection of undesirable sample components having a higher migration rate than the analyte molecules.

11. The integrated fluidic component according to claim 9, wherein said at least one further side channel is operated in order to actuate a sequence of gels independently of each other.

12. The integrated fluidic component according to claim 7, wherein the pore size, chemical composition and/or pH value of the gels vary within the sequence of different gels or a gradient of gels.

13. The integrated fluidic component according to claim 1, wherein the component comprises a side channel that is connectable to an external dosage system for incorporation of the gel into the electrophoretic gel separation section.

14. The integrated fluidic component according to claim 1, wherein the receptor device may be operated in order to carry out a hybridization experiment.

15. The integrated fluidic component according to claim 1, wherein the receptor device detects the presence and/or the concentration of nucleic acid molecules from viruses and/or bacteria present in the cell lysate or cell mixture.

16. The integrated fluidic component according to claim 1, wherein the receptor device detects the presence and/or the concentration of ribonucleic acid molecules from a non-human species in the cell lysate or mixture sample from a human body fluid.

17. The integrated fluidic component according to claim 1, wherein the component further comprises at least one integrated conditioning device for treating the sample and/or for treating the purified ribonucleic acid molecules.

18. The integrated fluidic component according to claim 17, wherein the conditioning device comprises a disruption device for disrupting the sample in the sample chamber.

19. The integrated fluidic component according to claim 18, wherein the disruption device is operated in order to carry out cell lysis.

20. The integrated fluidic component according to claim 19, wherein the sample chamber has at least one electrode for carrying out the cell lysis.

21. The integrated fluidic component according to claim 20, wherein said at least one electrode is formed by electrodes with a coplanar structure.

22. The integrated fluidic component according to claim 20, wherein said at least one electrode comprises a plurality of electrodes, which are positioned in different planes.

23. The integrated fluidic component according to claim 17, wherein thermal cell lysis occurs by application of an alternating current.

24. The integrated fluidic component according to claim 1, wherein the receptor device is in the form of an independent-module which can be inserted into the collecting chamber before a measurement.

25. The integrated fluidic component according to claim 1, wherein a movement direction of the sample runs through the gel separation section transversely to a detection layer of the integrated receptor device.

26. The integrated fluidic component according to claim 25, wherein the separation section is conically shaped and the sample chamber has a larger volume than the collecting chamber.

27. A method for purifying ribonucleic acid molecules by means of an integrated fluidic component, which comprises the following steps:
providing the fluidic component of claim 1;
filling the sample chamber positioned on the integrated fluidic component with a sample containing the ribonucleic acid molecules, the sample being a cell lysate or a cell mixture;
transporting the sample along the electrophoretic gel separation section positioned on the integrated fluidic component, wherein the electrophoretic gel separation section is directly connected with the sample chamber, so that the sample is purified directly by electrophoretic separation, and wherein the gel separation section is adapted to separating ribonucleic acid molecules from the sample;
collecting the purified ribonucleic acid molecules in the collecting chamber positioned on the integrated fluidic component; and
detecting the presence and/or the concentration of the purified ribonucleic acid molecules by means of the integrated receptor device on the microfluidic component.

28. The method according to claim 27, wherein the receptor device comprises a detection layer structured as an array for selectively binding the purified ribonucleic acid molecules.

29. The method according to claim 27, wherein the receptor device optically detects selectively bound ribonucleic acid molecules, by means of fluorescence.

30. The method according to claim 27, wherein the electrophoretic gel separation section is formed by a sequence of gels or a gradient of gels, which vary in their pore size, their chemical composition and/or their pH value.

31. The method according to claim 27, wherein the electrophoretic gel separation section has at least one side channel, which may be actuated by at least one additional electrode.

32. The method according to claim 27, wherein said at last one side channel is formed so that it may be operated for a pre-separation of undesired sample components, which have a higher migration rate than the ribonucleic acid molecules.

33. The method according to claim 27, wherein the cell mixture contains viruses and/or bacteria to be detected.

34. The method according to claim 27, wherein the sample is a human body fluid and the ribonucleic acid molecules are a component of non-human species.

35. The method according to claim 27, wherein the ribonucleic acid molecules contain transfer-messenger-RNA (tm-RNA).

36. The method according to claim 27, wherein the component further comprises at least one integrated conditioning device for treating the sample and/or for treating the purified ribonucleic acid molecules.

37. The method according to claim 36, wherein the conditioning device comprises a disruption device for disrupting the sample in the sample chamber.

38. The method according to claim 37, wherein the disruption device may be operated for carrying out cell lysis.

* * * * *